United States Patent [19]

Nakamura et al.

[11] 4,428,245

[45] Jan. 31, 1984

[54] APPARATUS FOR SAMPLING MOLTEN METAL

[75] Inventors: Hajime Nakamura, Kure; Junichi Iwamura; Yoshio Nakajima, both of Hiroshima; Masaji Hasegawa, Kure, all of Japan

[73] Assignee: Nisshin Steel Company Limited, Tokyo, Japan

[21] Appl. No.: 362,461

[22] Filed: Mar. 26, 1982

[30] Foreign Application Priority Data

Mar. 31, 1981 [JP] Japan ............................. 56-45869[U]
Jun. 24, 1981 [JP] Japan ............................. 56-93387[U]
Jun. 24, 1981 [JP] Japan ............................. 56-97959

[51] Int. Cl.³ ............................................. G01N 1/12
[52] U.S. Cl. ............................. 73/864.52; 73/864.58; 73/864.59
[58] Field of Search ........... 73/864.52, 864.54, 864.55, 73/864.56, 864.58, 864.59

[56] References Cited

U.S. PATENT DOCUMENTS

| 2,970,350 | 2/1961 | Feichtinger | 73/DIG. 9 |
| 3,315,529 | 4/1967 | Feichtinger | 73/864.52 |
| 3,369,406 | 2/1968 | Lowdermilk et al. | 73/864.52 |
| 3,859,857 | 1/1975 | Falk | 73/864.59 |
| 4,007,640 | 2/1977 | Boron | 73/864.59 |
| 4,170,139 | 10/1979 | Narita et al. | 73/864.52 |

Primary Examiner—S. Clement Swisher
Attorney, Agent, or Firm—Webb, Burden, Robinson & Webb

[57] ABSTRACT

A vacuum sampling container of a refractory material which comprises a small diameter cylindrical section and a large diameter cylindrical section coaxially connected in mutual communication and is evacuated and sealed, the free end of said small diameter cylindrical section being provided with a portion thinned to the extent that it is broken by virtue of the heat and pressure of the molten metal when the vacuum sampling container is immersed in a molten metal is disclosed. Also a sampler comprising said vacuum sampling container and a protective tube therefor is disclosed.

12 Claims, 47 Drawing Figures

APPARATUS FOR SAMPLING MOLTEN METAL

TECHNICAL FIELD OF THE INVENTION

This invention relates to a sampling container and a sampling apparatus for sampling molten metal whereby sound samples can be taken with easy operation.

BACKGROUND OF THE INVENTION

In the course of smelting, refining and casting of metal, samples for analyses are frequently taken in order to collect information on the molten metal. As the sampler for molten metal, there have been known (1) samplers which take in molten metal by virtue of molten metal head (pressure); (2) combination type sampler combining an iron edit tube and a quartz tube which draw molten metal; (3) samplers which forcibly draw molten metal by pumping; (4) samplers which draw molten metal by means of a vacuum drawing pipe, etc.

All of these known samplers are practically used and each of them has its respective advantage, but all have in common the disadvantage that samples of different shapes and quantities cannot be taken simultaneously.

For instance, in the course of refining of steel, for the purpose of analysis of the steel composition (chemical analysis, such as wet analysis and instrumental analysis such as photospectrometry) relatively large samples are taken using samplers of the above type (1) or type (2). On the other hand, for analysis of gaseous ingredients in steel, smaller samples in the shape of a small vial or a long pencil-like stick (usually 6 mm in diameter) are taken using samplers of the above type (3) or type (4). It is not convenient to take samples for gas analysis with samplers of types (1) and (2) from the view point of operation efficiency, and taking samples for chemical analysis with samplers of types (3) and (4) is not proper from the view point of the amount of samples. Therefore, people are obliged to use separate samplers to get samples for both analysis for chemical composition and analysis of gases respectively. This inevitably increases the frequency of sampling, which has an undesirable influence on the steelmaking operation, and also the consumption of many sampling containers raises the steelmaking cost.

When samplers of type (1) and (2) are used, cavities and bubbles are easily formed as the molten metal sample solidifies and therefore the samples taken are not always sound. Samplers of type (3) and (4) must be handled carefully and therefore these samplers are not versatile.

Under the circumstances, this invention is directed to a sampling container and an apparatus with which sound samples of different forms for both wet analysis and gas analysis can be taken simultaneously and exactly by simple operation.

In one aspect, this invention provides a vacuum sampling container which comprises a smaller diameter cylindrical section and a large diameter cylindrical section coaxially connected in mutual communication and evacuated and sealed, the free end of said small diameter cylindrical section being provided with a portion thinned to the extent that it is broken when the vacuum sampling container is immersed in a molten metal.

In another aspect, this invention provides a sampler for molten metal comprising a vacuum sampling container comprising a first small diameter cylindrical section and a large diameter cylindrical section connected coaxially in mutual communication and evacuated and sealed, the free end of said first small diameter cylindrical section being provided with a portion thinned to the extent that it is broken by virtue of the heat and pressure of the molten metal when the vacuum sampling container is immersed in a molten metal; a protective tube housing said vacuum sampling container and having an opening at the end thereof corresponding to the free end of said vacuum sampling container; and a connecting means secured to said vacuum sampling container which connects the integral body of said vacuum sampling container and the protective tube to a supporting rod for the sampler.

Now the invention is described in detail with reference to the attached drawings.

BRIEF DESCRIPTION OF THE ATTACHED DRAWINGS

FIGS. 1 through 4 represent an example of the vacuum sampling container in accordance with this invention.

FIGS. 8 through 11 show another example of the vacuum sampling container in accordance with this invention.

FIGS. 12 through 16 represent another modification of the vacuum sampling container.

FIGS. 17 through 21 represent still another modification of the vacuum sampling container.

FIGS. 22 through 25 represent still another modification of the vacuum sampling container.

FIGS. 26 through 29 represent still another modification of the vacuum sampling container.

FIGS. 30 through 34 represent still another modification of the vacuum sampling container.

FIGS. 35 through 39 represent still another modification of the vacuum sampling container.

DETAILED DESCRIPTION OF THE INVENTION

The container as shown in FIGS. 1 through 4 is a sealed container of a refractory material, quartz, for instance, comprising a large diameter cylindrical section 1 and a small diameter cylindrical section 2 which are coaxially connected in mutual communication. This hollow container is evacuated and is provided with a thinned portion 3 at the free end of the small diameter section 2, which is easily broken when the container is immersed in molten metal. The volume of the container is such as to hold 100–150 g of metal. The protruberance 4 at the free end of the large diameter section 1 is what remains after the container has been evacuated and heat-sealed. The container wall is of a uniform thickness except for the thinned portion 3. The thickness of the thinned portion is such that when the container is immersed in a molten metal, the portion is easily broken by virtue of the temperature and the pressure of the molten metal at the depth at which the container is immersed. The thickness is such that the portion is easily broken without any additional mechanical pressure applied at the sampling position, and the molten metal enters and fills the container up to the free end of the large diameter section. The sample taken in the small diameter section is suitable for gas analysis and the sample taken in the large diameter section is suitable for wet chemical analysis.

Figure 1:
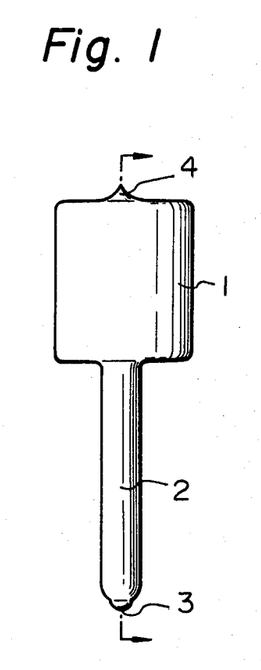
FIG. 1 is an elevational view.
Figure 2:
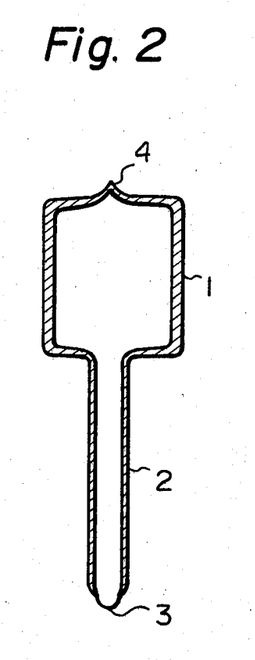
FIG. 2 is elevational cross section of the container along the line indicated with arrows in FIG. 1.
Figure 3:
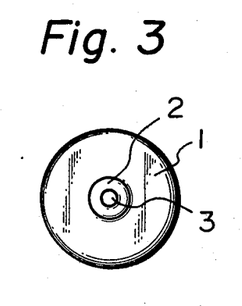
FIG. 3 is a bottom view of the container.
Figure 4:
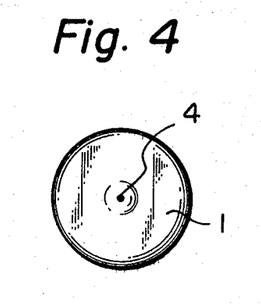
FIG. 4 is a plan view thereof.
Figure 5:
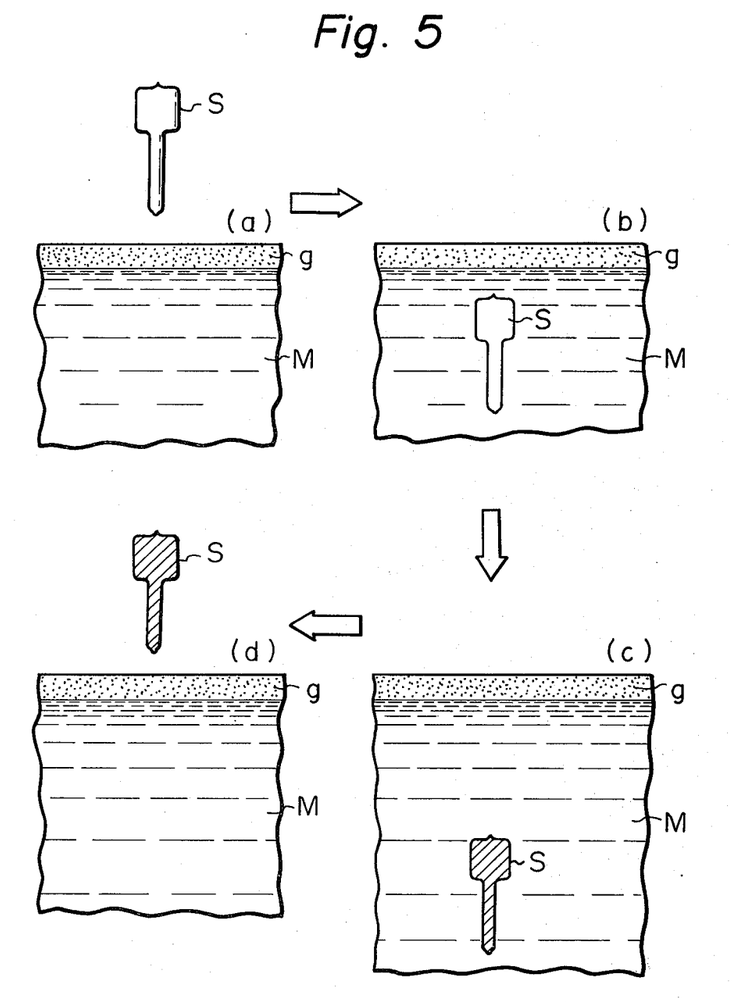
FIG. 5 shows steps in the sampling procedure in which the vacuum sampling container is used.

FIG. 5 schematically illustrates how the vacuum sampling container in accordance with this invention is used. A vacuum sampling container S is directed to the surface of a molten metal M with the small diameter cylindrical section ahead (Step a), and the vacuum sampling container is immersed in the molten metal (Step b). Then the thinned portion at the end of the small diameter cylindrical section is automatically broken by virtue of the heat (temperature) and the head (pressure) of the molten metal, and the molten metal is drawn into the container through the broken end (Step c). Finally the vacuum sampling container is lifted above the molten metal surface (Step d). Incidentally, g stands for the slag layer in FIG. 5. In the sampling using the vacuum sampling container of this invention, when the filled container S is lifted above the molten metal surface, the molten metal does not run out of the container through the broken portion. The reason therefor is that the container has been evacuated, and therefore no space is left therein after the molten metal has been drawn in, and the small diameter cylindrical section is rapidly cooled and thus the viscosity of the molten metal therein rapidly increases, and solidification of the molten metal at the broken portion proceeds instantaneously. It is believed that these several factors work in combination to prevent spilling of the molten metal taken.

Figures 6, 7:
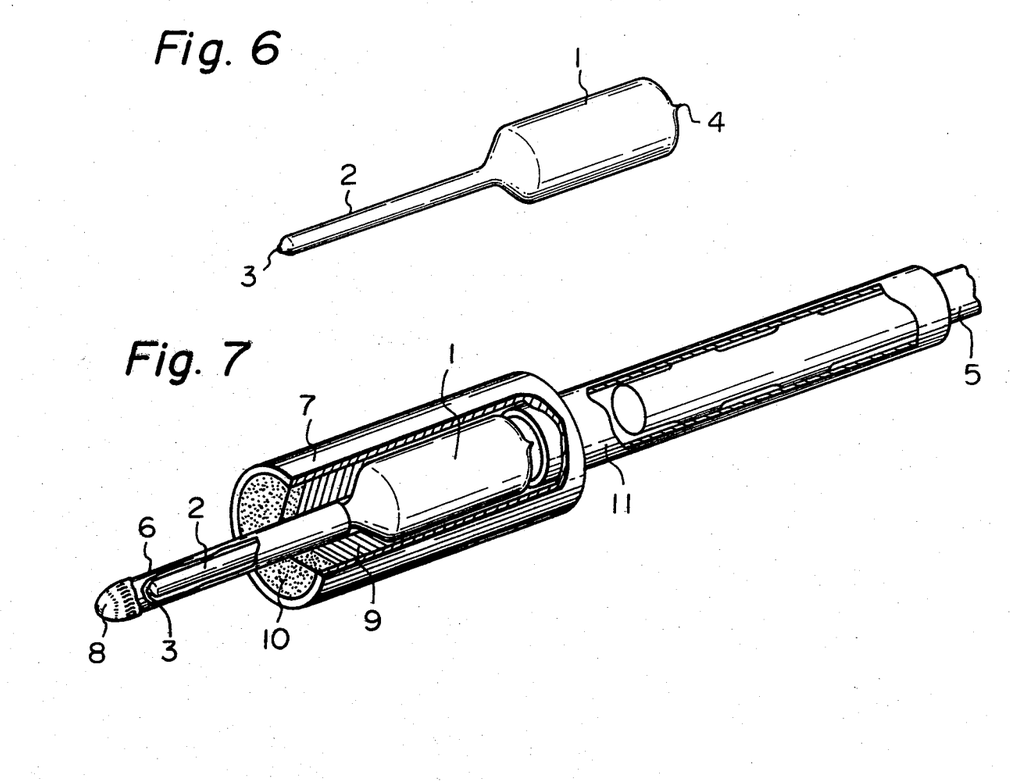
FIG. 6 is a perspective view of an example of the vacuum sampling container in accordance with this invention.
FIG. 7 is a partly broken perspective view showing the container as shown in FIG. 6 in combination with a protective tube and a supporting rod.
Figure 8:
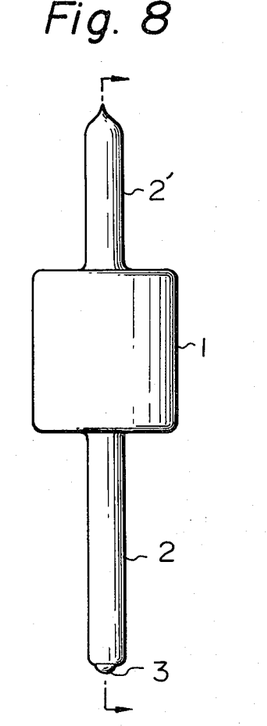
FIG. 8 is an elevational view.
Figure 9:
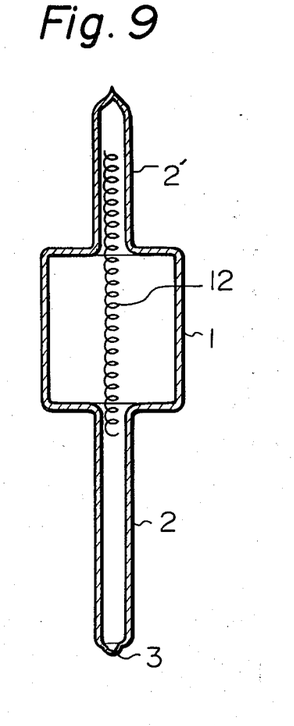
FIG. 9 is an elevational cross section of the container along the line indicated with arrows in FIG. 8.
Figure 10:
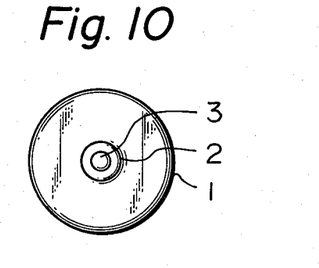
FIG. 10 is a bottom view of the container.
Figure 11:
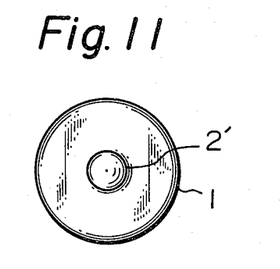
FIG. 11 is a plan view thereof.
Figures 12, 13A:
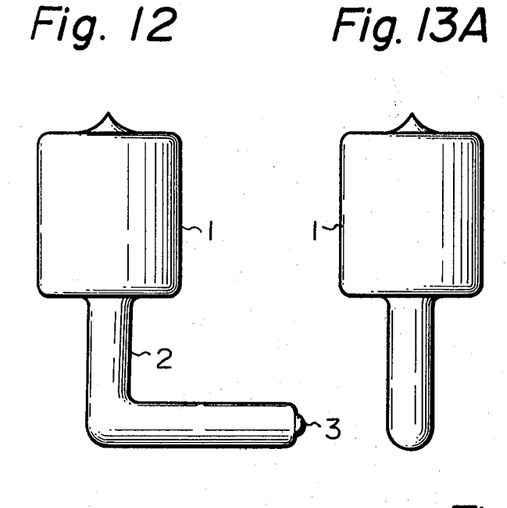
FIG. 12 is a front view.
FIG. 13(A) is a left side view and FIG. 13(B) is a right side view.
Figure 13B:
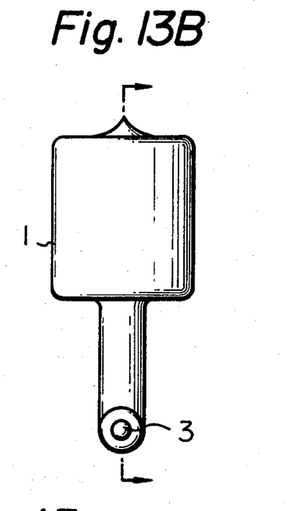
Figure 14:
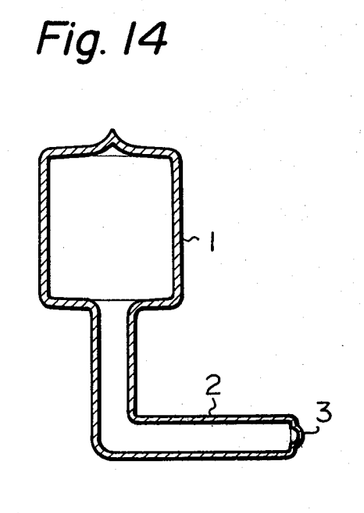
FIG. 14 is a cross section along the line indicated with arrows in FIG. 13(B).
Figure 15:
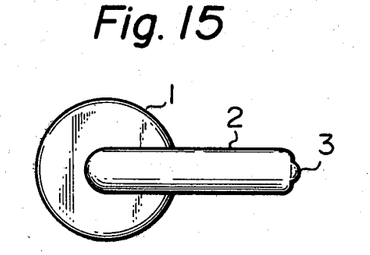
FIG. 15 is a bottom view and FIG. 16 is a plan view.
Figure 16:
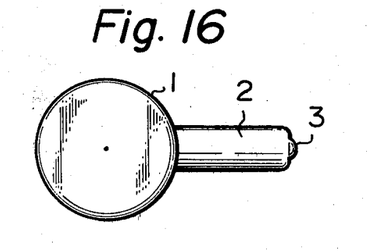
Figures 17, 18A, 18B, 19, 20, 21:
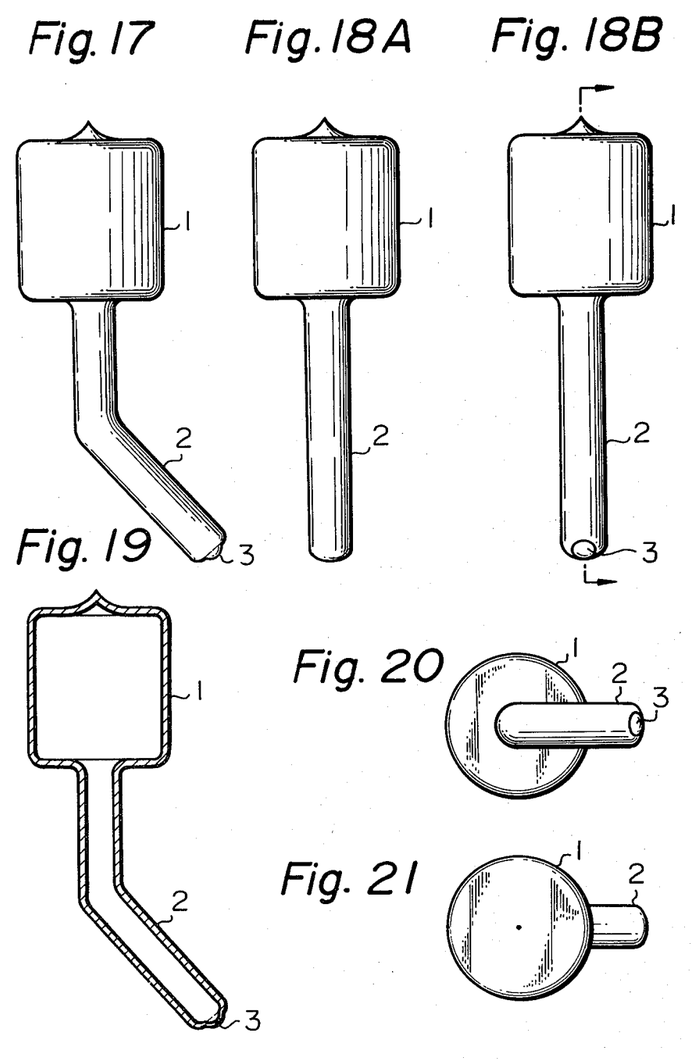
FIG. 17 is a front view.
FIG. 18(A) is a left side view and FIG. 18(B) is a right side view.
FIG. 19 is a cross section along the line indicated with arrows in FIG. 18(B).
FIG. 20 is a bottom and FIG. 21 is a plan view.
Figure 22:
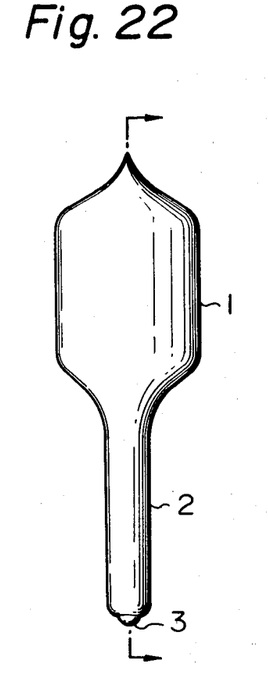
FIG. 22 is a front view.
Figure 23:
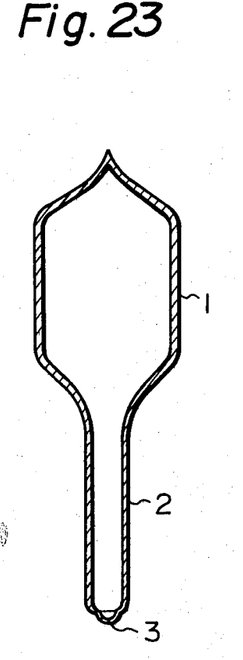
FIG. 23 is a cross section along the line indicated with arrows in FIG. 22.
Figure 24:
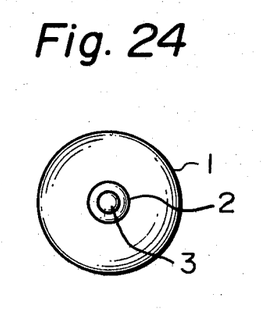
FIG. 24 is a bottom view and FIG. 25 is a plan view.
Figure 25:
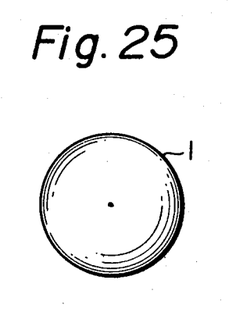
Figure 26:
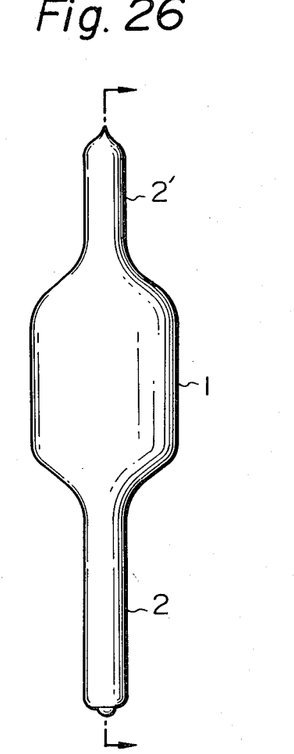
FIG. 26 is an elevational view.
Figure 27:
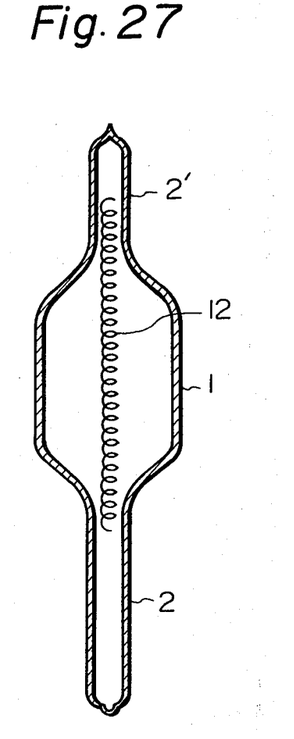
FIG. 27 is a cross section along the line indicated with arrows in FIG. 26.
Figure 28:
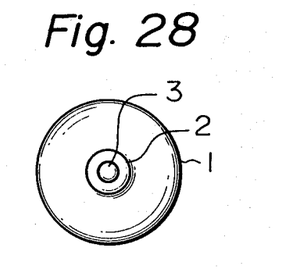
FIG. 28 is a bottom view and FIG. 29 is a plan view.
Figure 29:
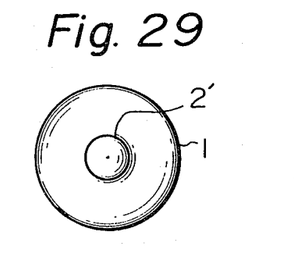
Figures 30, 31A:
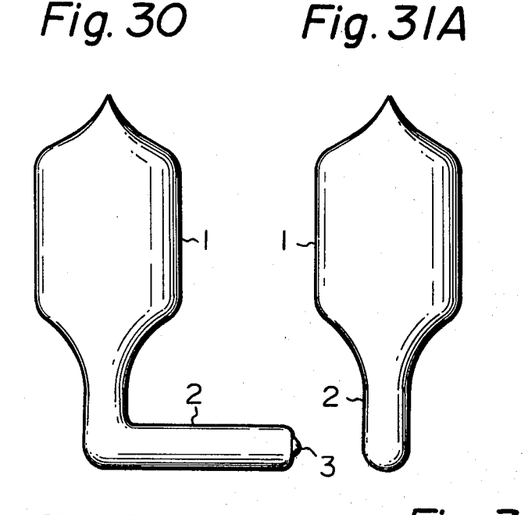
FIG. 30 is a front view.
FIG. 31(A) is a left side view and FIG. 31(B) is a right side view.
Figure 31B:
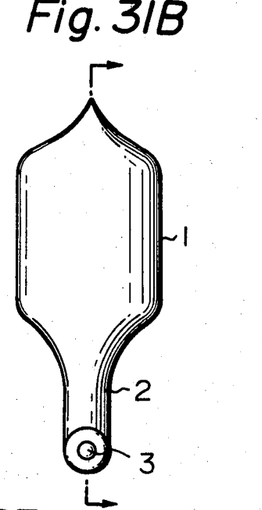
Figure 32:
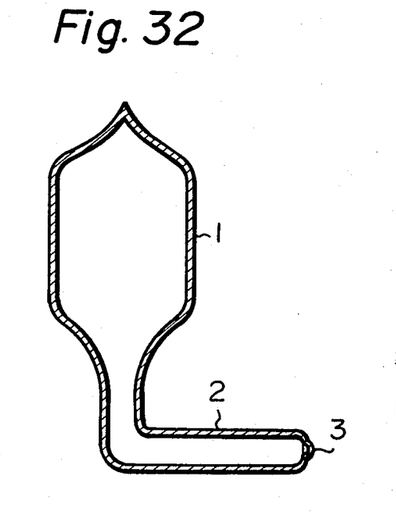
FIG. 32 is a cross section along the line indicated with arrows in FIG. 31(B).
Figure 33:
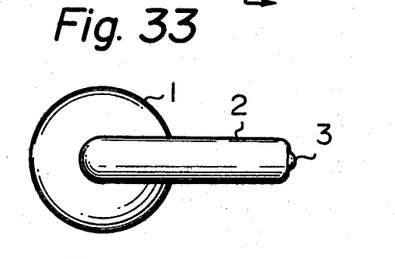
FIG. 33 is a bottom view.
Figure 34:
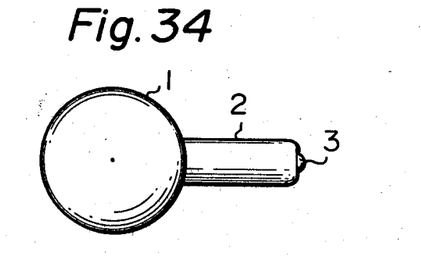
FIG. 34 is a plan view.
Figures 35, 36A, 36B, 37, 38, 39:
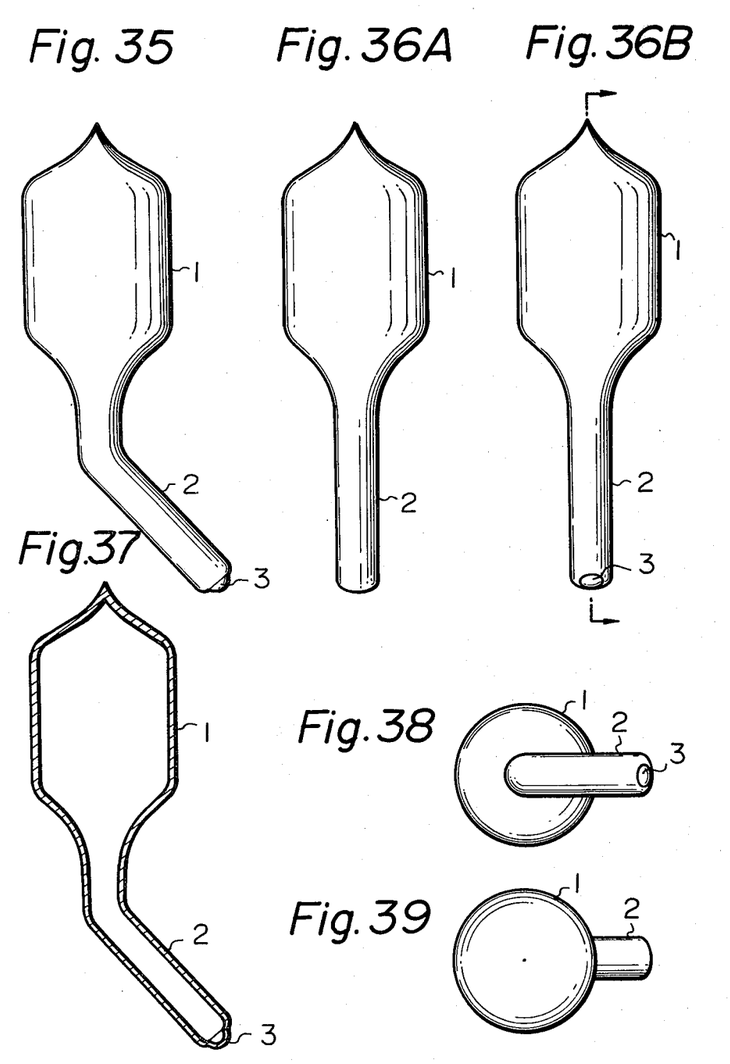
FIG. 35 is a front view.
FIG. 36(A) is a left side view and FIG. 36(B) is a right side view.
FIG. 37 is a cross section along the line indicated with arrows in FIG. 36(B).
FIG. 38 is a bottom view.
FIG. 39 is a plan view.

In the actual operation, sampling is conveniently carried out by supporting the vacuum sampling container in a protective tube, which is connected to a sampling rod as shown in FIG. 7. In FIG. 7, the container as shown in FIG. 6 is protected by two protective tubes. The small diameter cylindrical section 2 is covered by a first protective tube 6, the large diameter section 2 is covered by a second protective tube 7, and the first protective tube 6 and the second protective tube 7 are fixed by means of a refractory cement 10. Thus all the surface of the vacuum sampling container as shown in FIG. 6 is protected. The free end of the first protective tube 6 covering the small diameter section of the vacuum sampling container, that is, the end of the first protective tube corresponding to the free end of the small diameter cylindrical section of the container, has an opening through which the molten metal can run.

Protective tubes are conveniently made of paper. For instance, convoluted kraft paper is suitable. The first protective tube 6 is connected with the second protective tube 7 by means of a refractory cement 10 as mentioned above after the cavity in the second protective tube 7 is filled with split packing 9. When immersed in molten metal, the protective tubes of paper are instantaneously carbonized and remain rigid bearing the vacuum sampling container therein and being supported by the sampling rod. Even when lifted above the molten metal surface, the protective tubes do not burn in the atmosphere above the molten bath. A cap 8 may be placed on the opening of the protective tube 6 as shown in FIG. 7. This cap works to protect the thinned portion 3 of the vacuum sampling container from contamination with the slag and possible damage by the slag layer when it penetrates through the slag layer. The cap is made of a thin layer which easily melts when it is immersed in molten metal. A suitable material is selected by considering the melting temperature of the molten metal a sample of which is to be taken. Practically, when molten steel is sampled, steel is used, and when molten copper is sampled, copper is used. Contamination with slag need not be considered, that is, molten metal in a casting mold is sampled for instance, the cap 8 is dispensable.

The amount of a sample taken is 100–150 g as mentioned above. In contrast, the weight of the cap is 0.5–1 g. Therefore, the cap has little influence on the composition of the sample to be taken, although the cap dissolves in close proximity to the molten metal to be sampled.

FIG. 7 shows an embodiment in which a protective tube comprising two sections of different diameters. A one section protective tube can be used instead of a two section tube, of course. A slag-breaking member can be attached at the end of the protective tube, if the protective tube has to penetrate a hard slag layer.

The protective tube 7 is connected to a sampling rod, by means of a connecting member 11, which is a hollow cylinder, as shown in FIG. 7. It may be made of paper like the protective tubes mentioned above. The connecting member 11 has an inside diameter equal to the outside diameter of the sampling rod 5. Usually the sampling rod has a plurality of ridges or fins as seen in FIG. 7, which frictionally contact the inside wall of the connecting member 11. When sampling molten steel in a refining furnace or a ladle, it is all right if a mechanism which lifts and lowers the sampling rod is provided over the refining furnace or a ladle. Automation of sampling is also easily effected.

FIGS. 8 through 11 show a vacuum sampling container which is used for an advanced method of sampling according to this invention. This sampling container is substantially the same as that represented by FIGS. 1 through 4 except that a second small diameter cylindrical section 2' is provided in the large diameter cylindrical section on the side opposite to the first small diameter cylindrical section 2, and a deoxidizing agent 12 is placed in the second small diameter cylindrical section and the large diameter section. The operation of this vacuum sampling container is quite the same as the previously described embodiment. In this embodiment, it is possible to take a sounder sample from a molten steel which is not yet deoxidized. When the thinned portion 3 is broken and molten metal is drawn in, the molten metal solidifies after being deoxidized in the second small diameter cylindrical section 2' and the large diameter cylindrical section 1. Therefore a sounder sample free from pin holes and porosities can be taken. In this case, the first small diameter cylindrical section works only as a guide passage for molten metal. The lump sample is taken from the large diameter cylindrical section and the stick sample is taken from the second small diameter cylindrical section. The metal solidified in the first small diameter section is not always used for analysis. As the deoxidizing agent, aluminum will be suitable. A coil of aluminum wire, an aluminum wire bent in several folds, a folded aluminum foil, etc. can suitably be used. They are placed in the large diameter cylindrical section so that a portion thereof extends into the second small diameter cylindrical section.

FIGS. 12 through 16 show another embodiment of the vacuum sampling container used for the method of sampling in accordance with this invention. In this embodiment, the small diameter cylindrical section is bent generally at a right angle. Therefore this is conveniently used for sampling from a mold for continuous casting where obstacles are usually located immediately above the mold. That is, the vacuum sampling container is horizontally held above the molten metal and the small diameter cylindrical section is immersed in the molten metal by rotating the supporting rod.

In the embodiment shown in FIGS. 17 through 21, the small diameter cylindrical section 2 is bent at an obtuse angle. With this sampling container, sampling can be carried out at an angle from above.

In the four embodiments of the vacuum sampling container shown in FIGS. 22 through 39, the connection of the large diameter cylindrical section and the small diameter cylindrical section is smoothly sloping or funnel-shaped. By employment of such configuration, the sampling container is easily formed when quartz is used, and at the same time sounder samples can be taken. The embodiment shown in FIGS. 22 through 25 is a modification of the embodiment shown in FIGS. 1 through 4. The embodiment shown in FIGS. 26 through 29 is a modification of the embodiment shown in FIGS. 8 through 11. The embodiment shown in FIGS. 30 through 34 is a modification of the embodiment shown in FIGS. 12 through 16. The embodiment shown in FIGS. 35 through 39 is a modification of the embodiment shown in FIGS. 17 through 21. The sampling containers of these embodiments are used in substantially the same way as explained with respect to the previously described embodiments.

The embodiments illustrated in the drawings are only exemplification. Dimension and configuration of the small diameter cylindrical section and the large diameter cylindrical section can be modified at the discretion in consideration of properties of molten metal and operation in analysis, etc. Only the fundamental requirements are that the thinned portion is provided at the free end of the small diameter cylindrical section and the diameter and length of the small diameter cylindrical section and area of the thinned portion are determined so that the molten metal taken in the sampling container does not run out when the sample container is immersed in the molten metal and vertically lifted above the surface of the molten metal.

Figure 40:
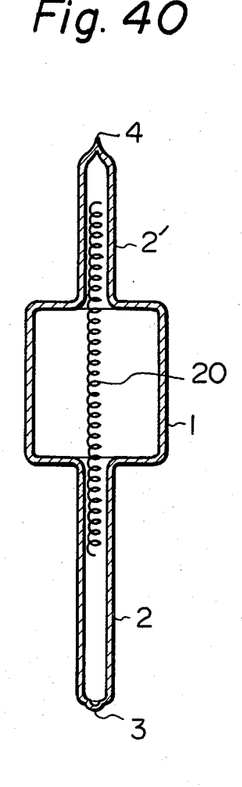
FIG. 40 is a cross sectional view of still another modification of the vacuum sampling container of this invention.
Figures 41, 42:
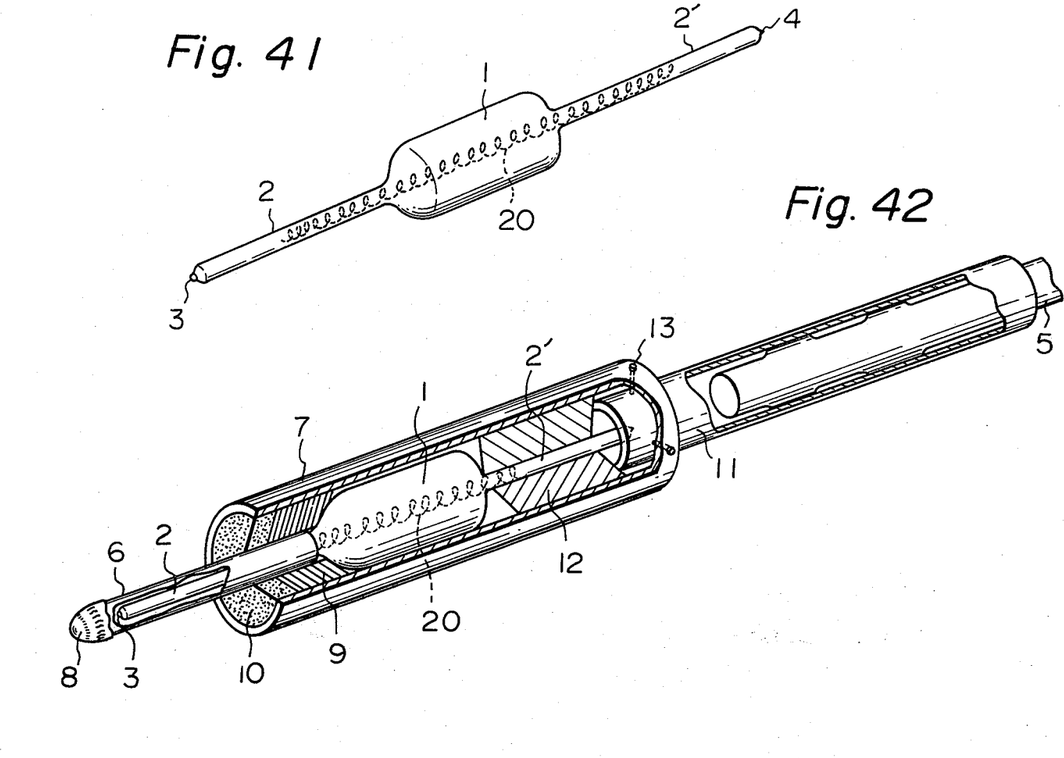
FIG. 41 is a perspective view of still another modification of the vacuum sampling container of this invention.
FIG. 42 is a partly broken perspective view showing a modification of the container in combination with a protective tube and a supporting rod as shown in FIG. 7.

In FIG. 40, a modification of the embodiment of the vacuum sampling container shown in FIGS. 8 through 11 is shown. In FIG. 41, a modification of the embodiment of the vacuum sampling container shown in FIGS. 26 through 29. These modifications are substantially the same as the corresponding fundamental embodiments. They differ only in that a longer aluminum coil is used and it is placed in the small diameter cylindrical section, too. When these sampling containers are used, molten metal samples held in the small diameter cylindrical sections 2 and 2' are suitable for gas analysis, and the sample held in the large diameter cylindrical section is suitable for wet chemical analysis.

In FIG. 42, a modification of the embodiment of the sampling apparatus shown in FIG. 7 and explained with respect to FIG. 7 is shown. This modification is substantially the same as the embodiment of FIG. 7. It is different only in that the connecting member 11 is secured to the protective tube 7 by means of a plurality of pins 13.

Figure 43:
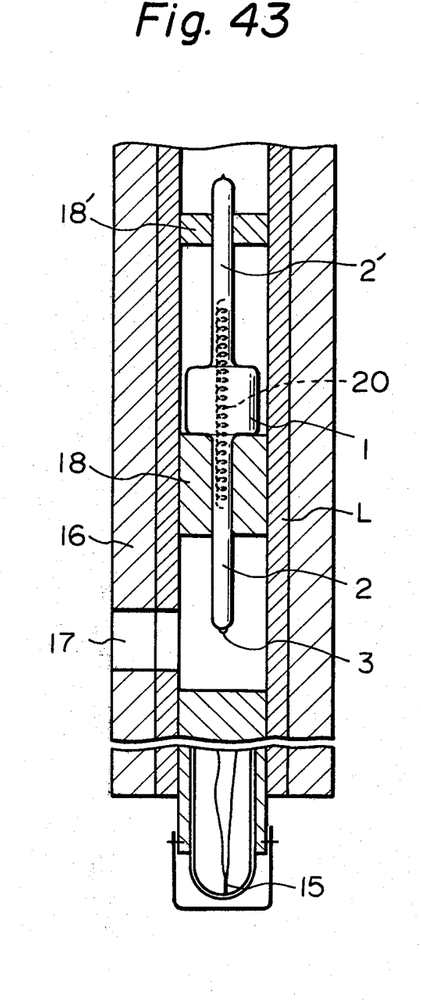
FIG. 43 is a cross sectional view representing another embodiment of the container in combination with a temperature-measuring sub-lance.

FIG. 43 represents another mode of use of the vacuum sampling container of this invention. A vacuum sampling container 1 is placed at the end of a temperature-measuring sub-lance L. As seen in FIG. 43, a temperature-measuring thermocouple 15 is mounted at the tip of the lance L. In the hollow of the lance, a vacuum sampling container 1 is housed, supported by a supporting member 18 and 18'. Near the free end of the small diameter cylindrical section of the vacuum sampling container 1, an opening 17 is provided through the protective tube 16 and the lance wall L. When the lance is immersed in molten metal, the molten metal penetrates into the hollow and the thinned portion 3 of the vacuum sampling container is broken by virtue of the heat and pressure of the molten metal. Thus the moltel metal is sampled as described above. In FIG. 43, a vacuum sampling container as shown in FIG. 41 is used.

Now the invention is illustrated by way of working examples and comparative examples.

Samples were taken from a molten steel by using the vacuum sampling container and the sampler including such vacuum sampling container in accordance with this invention and by the conventional devices. The results are summarised in the following table.

TABLE

| | Sampling | Composition of Steel (%) | | | | | | | Gases in Steel (ppm) | | |
|---|---|---|---|---|---|---|---|---|---|---|---|
| | | C | Si | Mn | P | S | sol. Al | insol. Al | Sampling | T.O. | T.N. |
| A | This invention | 0.05 | 0.01 | 0.30 | 0.012 | 0.013 | 0.016 | 0.003 | This invention | 88 | 29 |
| | Drawing with an alumina crucible | 0.05 | 0.02 | 0.29 | 0.012 | 0.013 | 0.020 | 0.005 | Sucking with a syringe | 90 | 29 |
| B | This invention | 0.08 | 0.01 | 0.27 | 0.013 | 0.014 | 0.081 | 0.006 | This invention | 78 | 21 |
| | Drawing with a quartz tube in an iron edit tube | 0.07 | 0.01 | 0.25 | 0.014 | 0.014 | 0.079 | 0.006 | Vacuum drawing | 77 | 22 |
| C | This invention | 0.07 | tr. | 0.28 | 0.012 | 0.013 | 0.050 | 0.004 | This invention | 87 | 25 |
| | Drawing with an iron edit tube | 0.07 | tr. | 0.27 | 0.011 | 0.012 | 0.048 | 0.004 | Sucking with a syringe | 85 | 24 |
| D | This invention | 0.09 | tr. | 0.35 | 0.013 | 0.012 | 0.035 | 0.003 | This invention | 48 | 13 |
| | Drawing with an iron edit tube | 0.09 | tr. | 0.33 | 0.012 | 0.013 | 0.032 | 0.003 | Vacuum drawing | 49 | 15 |
| E | This invention | 0.10 | 0.01 | 0.36 | 0.012 | 0.011 | 0.028 | 0.002 | This invention | 44 | 16 |
| | Drawing with a quartz tube in an iron edit tube | 0.11 | tr. | 0.36 | 0.013 | 0.011 | 0.030 | 0.003 | Sucking with a syringe | 45 | 18 |

The used vacuum sampling containers were made of quartz and were of the shape shown in FIG. 7. The diameter of the small diameter section thereof was 8 mm and that of the large diameter section was 29 mm. The total length of the container was 175 mm and the length of the first small diameter section was 105 mm and that of the large diameter section was 70 mm. A coiled aluminum wire was inserted in the section small diameter cylindrical section and the large diameter cylindrical section. The vacuum sampling containers were supported by the protective tube as shown in FIG. 7 and connected to a sampling rod.

After a sample had been taken, the container was broken and the sample from the large diameter cylindrical section was analyzed to determine the compositions of the steel and the sample from the small diameter cylindrical section was analyzed to determined contents of oxygen and nitrogen.

The conventional sampling methods employed were drawing with an alumina crucible, drawing with iron edit and combined use of iron edit and quartz tube. For gas analysis, drawing with plunger and vacuum drawing were employed.

the steel compositions obtained from the samples taken by the devices of this invention exhibited approximately the same levels of the contents as the results obtained from the samples taken by the conventional devices, although the Mn content in samples A, B, C and D was slightly higher than the samples taken by conventional devices, and the sol. Al content in Sample A (0.016%) is somewhat lower than that (0.020%) of the sample taken by the conventional method (drawing with alumina crucible).

INDUSTRIAL APPLICABILITY

As has been explained above, in accordance with this invention, sampling of molten metal can be carried out by the simple operation of lowering and lifting of a vacuum sampling container. Even in the sampling of a molten steel at a temperature as high as 1700° C., sound samples free from porosities, bubbles and cavities can be obtained in a very short period of time. The sample is provided with a stick portion suitable for gas analysis and a lump portion suitable for wet chemical analysis.

In the prior art methods, a gas analysis sample and a wet chemical analysis sample are taken separately. That is to say, sampler cannot be taken at the same spot at the same time, and therefore correct and comprehensive information at a point of time cannot be obtained. This invention removes such disadvantages. A sample once drawn into a sampling container is not contaminated with the slag layer or other materials near the surface of the liquid phase when the container is lifted therethrough. Thus quite reliable samples can be obtained. With the apparatus of this invention more reliable information about molten metal can be obtained more speedily then with the prior art apparatus, and thus this invention greatly contributes to production of metallic materials.

We claim:

1. A vacuum sampling container which comprises a small diameter cylindrical section and a large diameter cylindrical section coaxially connected in mutual communication and evacuated and sealed, the free end of said small diameter cylindrical section being provided with a portion thinned to the extent that it is broken when the vacuum sampling container is immersed in a molten metal, said container being quartz.

2. The vacuum sampling container as claimed in claim 1, which further comprises a second small diameter cylindrical section provided coaxially in communication on the opposite side of the large diameter cylindrical section to the first small diameter cylindrical section.

3. The vacuum sampling container as claimed in claim 1 or 2, wherein the first small diameter cylindrical section is bent approximately at a right angle.

4. The vacuum sampling container as claimed in claim 1 or 2, wherein the first small diameter cylindrical section is bent at an obtuse angle.

5. The vacuum sampling container as claimed in claim 3, wherein a deoxidizing agent is inserted beforehand.

6. The vacuum sampling container as claimed in claim 4, wherein a deoxidizing agent is inserted beforehand.

7. The vacuum sampling container as claimed in claim 5, wherein the deoxidizing agent is a wire, coil or foil of aluminum.

8. The vacuum sampling container as claimed in claim 6, wherein the deoxidizing agent is a wire, coil or foil of aluminum.

9. A sampler for molten metal comprising a vacuum sampling container comprising a first small diameter cylindrical section and a large diameter cylindrical section connected coaxially in mutual communication and evacuated and sealed, the free end of said first small diameter cylindrical section being provided with a portion thinned to the extent that it is broken by virtue of the heat and pressure of the molten metal when the vacuum sampling container is immersed in a molten metal, said container being quartz; a protective tube housing said vacuum sampling container and having an opening at the end thereof corresponding to the free end of said vacuum sampling container; and a connecting means secured to said vacuum sampling container which connects the integral body of said vacuum sampling container and the protective tube to a supporting rod for the sampler.

10. The sampler as claimed in claim 9, wherein the protective tube comprises a first tube protecting the small diameter cylindrical section of the vacuum sampling container and a second tube protecting the large diameter cylindrical section of the vacuum sampling container, said first tube being telescopically engaged with the second tube.

11. The sampler as claimed in claim 9 or 10, wherein the protective tube is made of convoluted paper.

12. The sampler as claimed in claim 9 or 10, wherein the vacuum sampling container is provided with a second small diameter cylindrical section provided on the large diameter cylindrical section on the opposite side of the first diameter small cylindrical section coaxially in communication with the large diameter cylindrical section.

* * * * *